United States Patent [19]

Garfield

[11] Patent Number: 5,546,953
[45] Date of Patent: Aug. 20, 1996

[54] METHOD AND APPARATUS FOR THE RECORDING AND ANALYSIS OF UTERINE ELECTRICAL ACTIVITY FROM THE ABDOMINAL SURFACE

[75] Inventor: Robert E. Garfield, Friendswood, Tex.

[73] Assignee: Board of Regents, The University of Texas System, Austin, Tex.

[21] Appl. No.: 246,214

[22] Filed: May 19, 1994

[51] Int. Cl.$^6$ .................................................. A61B 5/04
[52] U.S. Cl. ........................................ 128/733; 128/778
[58] Field of Search ................................ 128/733, 738, 128/774, 778, 782

[56] References Cited

U.S. PATENT DOCUMENTS

| | | | |
|---|---|---|---|
| 4,256,118 | 3/1981 | Nagel | 128/733 |
| 4,396,019 | 8/1983 | Perry, Jr. | 128/733 |
| 4,967,761 | 11/1990 | Nathanielsz | 128/733 |
| 5,154,177 | 10/1992 | Eisman et al. | 128/642 |
| 5,301,680 | 4/1994 | Rosenberg | 128/733 |
| 5,373,852 | 12/1994 | Harrison et al. | 128/733 |
| 5,397,344 | 5/1995 | Garfield et al. | 607/138 |

FOREIGN PATENT DOCUMENTS 2601254  1/1988  France .

OTHER PUBLICATIONS

Margue et al., "Uterine EHG Processing for Obstetrical Monitoring," *IEEE Transactions on Biomedical Engineering*, BME–33(12):1182–1186, Dec. 1986.

Pajntar et al., "Electromyography of the Human Uterus," IEEE Engineering in Medicine and Biology Society 10th Annual International Conference, New Orleans, Louisiana, vol. 10, Nov. 1988.

Tepavac and Nikolić, "A Portable 8 Channel Surface EMG Recording System," *Proceedings of the Annual International Conference of the IEEE ENgineering in Medicine and Biology Society*, 14:1433–1434, Oct.–Nov. 1992.

Wolfs and van Leeuwen, "Electromyographic observations on the human uterus during labor," *Acta Obstetricia et Gynecologica Scandinavica*, Supplement 90:22–42, 1979.

Devedeux, Marque, Duchêne, Germain, Mansour, "Uterine Electromyography: A Critical Review," *Am. J. Obstet. Gynecol.* 169:1636–1653, 1993.

Wolfs and Van Leeuwen, "Electromyographic observations on the Human Uterus during Labour," *Acta Obstet. Gynecol. Scand.* [Suppl.] 90:1–62.

Garfield, Blennerhassett, Miller, "Control of Myometrial Contractility: Role and Regulation of Gap Junctions," *Oxford Rev. Reprod. Biol.* 10:436–490, 1988.

Dill and Maiden, "The Electrical Potentials of the Human Uterus in Labor," *Am. J. Obstet. Gynecol.* 52:735–745, 1946.

Steer, "The Electrical activity of the Human Uterus in Normal and Abnormal Labor," *Am. J. Obstet. Gynecol.* 68:867–890, 1954.

Halliday and Heyns, "Uterine Activity and Electrical Response," *J. Obstet. Gynaec. Brit. Emp.* 62:155–161, 1955.

Hon and Davis, "Cutaneous and Uterine Electrical Potentials in Labor–an Experiment," *Obstet. Gynec.* 12:47–53, 1958.

Csapo, Chapter 43, "Force of Labor," *Principles and Practices of Obstetrics and Perinatology*, Ed. L. Iffy and H. A. Kaminetzky Publishing, John Wiley and Sons, 761–799, 1981.

Marshall, "Regulation of Activity in Uterine Smooth Muscle," *Physiol. Rev.* 42:213–227, 1962.

Garfield, Chapter 3, "Role of Cell–to–Cell Coupling in Control of Myometrial Contractility and Labor," *Control of Uterine Contractility*, Ed. R. E. Garfield and T. Tabb, CRC Press, 39–41, 1994.

*Primary Examiner*—Max Hindenburg
*Attorney, Agent, or Firm*—Arnold, White & Durkee

[57] ABSTRACT

A method and apparatus for recording and analyzing uterine electrical and mechanical activity from the abdominal surface. Electrodes are applied to the abdominal surface of a patient, and electromyographic signals produced by the electrodes are digitized, stored and analyzed to assess uterine electrical activity. Assessment of the function of other smooth muscle organs, for example the bladder and lower gastrointestinal tract is also contemplated.

19 Claims, 12 Drawing Sheets

METHOD AND APPARATUS FOR THE RECORDING AND ANALYSIS OF UTERINE ELECTRICAL ACTIVITY FROM THE ABDOMINAL SURFACE

BACKGROUND OF THE INVENTION

This invention relates to a method and apparatus for recording uterine or vaginal electrical activity. More specifically, the invention relates to a method and apparatus useful for determining the contractility of the uterus by recording spontaneous, mechanically or electrically stimulated, or drug-evoked electrical activity of the myometrium of the uterus from the abdominal or vaginal surface.

Presently there is no objective manner with which to evaluate the contractility of the uterus. This is true either in nonpregnant patients where hypercontractility is associated with dysmenorrhea or in pregnant patients where the uterus is sometimes active prior to term. Normally the uterus is quiescent in nonpregnant women and during most of pregnancy. However, at the end of pregnancy the myometrium undergoes a series of changes that lead to synchronous, rhythmic uterine contractions (labor). The diagnosis of labor is the most significant problem faced by obstetricians. In addition, preterm labor, which occurs in about 10% of pregnant patients, is difficult to diagnose. Frequently term or preterm labor require adjuvant therapy to either stimulate or inhibit contractility of the uterus.

Since there is some minor spontaneous uterine activity at all times during pregnancy, it is often not possible to distinguish between this physiological activity and term or preterm labor. The state of the cervix is commonly used as a predictor of labor. However, the softening of the cervix occurs relatively late in labor. In addition, labor and changes in the cervix can occur independently. Alternatively the frequency of contractions is used to diagnosis labor, sometimes recorded with a tocodynamometer. However, these methods give only crude subjective estimates of uterine contractility.

The uterus does not contract vigorously throughout most of pregnancy and this provides a tranquil environment for the growing fetus. At term the uterus normally begins to contract forcefully in a phasic manner (labor) to expel the fetus. Contractions of the uterus are directly proportional to the underlying electrical activity of the muscle. The frequency, duration and magnitude of a uterine contraction are directly proportional respectively to frequency of bursts of action potentials, the duration of a burst of action potentials, and the propagation (also referred to as conduction) of action potentials over the uterus and the recruitment of muscle cells. A similar situation exists in heart muscle although heart and uterine muscle are different with respect to structure and configuration of the action potentials. The action potentials are accompanied by the influx of calcium into the muscle cells to activate the contractile apparatus.

Thus, by recording uterine electrical activity one can assess the contractility of the myometrium. Similar technology is used to record cardiac electrical activity to determine the normal or abnormal function of the heart.

Many studies have previously recorded uterine myometrial electrical activity using electromyography (EMG) where electrodes are placed directly on the uterus. These studies show that the myometrium generates little electrical activity prior to labor but activity increases tremendously during labor reflecting the mechanical events. Studies of interest are demonstrated in publications by Csapo, Chapter 43, "Force of Labor," *Principles and Practice of Obstetrics and Perinatology*, Ed. L. Iffy and H. A. Kaminetzky Publishing, John Wiley and Sons 761–799, 1981; Garfield et al., "Control of Myometrial Contractility: Role and Regulation of Gap Junctions," Oxford Rev. Reprod. Biol. 10:436–490; 1988; Wolfs and Van Leeuwen, "Electromyography observations on the human uterus during labor," Acta Obstet. Gynecol. Scand. [Suppl.] 90:1–62, 1979; and more recently by Devedeux et al., "Uterine Electromyography: A Critical Review," Am J. Obstet. Gynecol, 169:1636–1653, 1993. One may measure and use uterine EMG activity by direct contact with the uterus to predict normal and abnormal uterine contractions. However, it is not practical to place electrodes directly on the uterus. To do this under the present level of understanding one must surgically implant electrodes on the uterine surface or introduce a catheter electrode through the vaginal canal and puncture the fetal membranes.

It would be desirable to record uterine EMG activity from the abdominal or vaginal surface. However, previous studies of electrical activity of the uterus recorded with electrodes placed on the abdominal surface have failed to record bursts of action potentials from the uterus and generally show no association of uterine electrical activity with contractility. Studies of interest are included in the above-noted publications by Wolfs and Van Leeuwen, and by Devedeux et al. Wolfs and Van Leeuwen summarized all studies prior to 1979 and concluded that "it has never been clearly shown that the potential fluctuations obtained by means of electrodes attached to the abdominal wall, do indeed represent the electrical activity of the uterus." (Page 7.) Similarly, Devedeux et al state that abdominal monitoring of uterine electrical activity "requires further investigation." (Page 1649.)

Part of the difficulty in interpretation of electrical activity recorded from the uterus lies in the fact many investigators, including Wolfs and Van Leeuwen and Devedeux et al. have failed to recognize that action potentials drive the uterus to contract. Action potentials are not responsible for contraction of some smooth muscle tissues such as airway muscle and some vascular muscles and therefore many researchers confound the uterus with other smooth muscle tissues. Thus, many of these studies have attempted to correlate electrical activity with mechanical contractions in order to show that electrical activity is responsible for contractions. However, no study has measured uterine and surface EMG simultaneously and correlated these to contractions. Furthermore, it is now clear (From publications by Marshall, "Regulation of Activity in Uterine Smooth Muscle," Physiol. Rev. 42:213–227, 1962; Csapo, Chapter 43, "Force of Labor," *Principles and Practice of Obstetrics and Perinatology*, Ed. by L. Iffy and H. A. Kaminetsky, John Wiley & Sons, 761–799, 1981; Garfield et al., "Control of Myometrial Contractility: Role and Regulation of Gap Junctions," Oxford Rev. Reprod. Biol, 10:436–490, 1988; Garfield, Chapter 3, "Role of cell-to-cell Coupling in Control of Myometrial Contractility and Labor," *Control of Uterine Contractility*, Ed. R. E. Garfield and T. Tabb, CRC Press, 39–81, 1994), that action potentials activate the uterus to contract and that by measuring uterine electrical activity one can indirectly estimate contractility.

SUMMARY OF THE INVENTION

The present invention presents a method and apparatus for recording uterine electrical activity from the surface of the abdomen or vagina for the purpose of diagnosing contractile patterns of the uterus in pregnant and nonpregnant patients.

A feature of the present invention is the measurement in vivo of the electrical and therefore the mechanical activity of uterine muscle tissue, to produce a more quantitative, comprehensive and analytical framework of the tissue by transferring information from the tissue to a computer memory for automatic analysis and for display on a monitor for assessment by an attending physician or other party interested in monitoring the tissue.

The present invention is applicable to a wide range of obstetrical, gynecological and other conditions. One such application is defining the state of the uterus during term and preterm labor. Another application is monitoring the nonpregnant uterus for indication of conditions such as infertility and uterine pathology in cycling women. The method and apparatus are also valuable for use in connection with other tissues other than the uterus such as tests of bladder function during urination or similarly, evaluation of the bowels during defecation.

In accordance with an embodiment of the invention, recording electrodes are placed at various points on the abdominal surface of a pregnant patient. The electrodes are connected to an amplifier to amplify the electrical signals and in turn the amplifier is linked to a computer for analysis and display of the signals. The signals detected by the electrodes are surveyed to provide measurements indicative of spontaneous electrical activity. The computer contains software to facilitate this analysis of the signals.

The above described electrodes may alternatively be placed on the vaginal wall. This may be particularly useful for monitoring electrical activity in early pregnancy and in nonpregnant women where the uterus is small and not likely to produce strong EMG signals that propagate to the abdominal surface, but are transferred down the reproductive tract to the vagina.

In particular, the present invention contemplates a method of characterizing uterine electrical activity by applying electrodes to the abdominal surface of a patient, storing electromyographic signals produced by the electrodes, and then analyzing the stored electromyographic signals in order to characterize uterine activity of the patient based on the analysis.

The invention also contemplates the stimulation of the vagina of the patient while the electromyographic signals are being stored. This stimulation permits the assessment from the stored electromyographic signals for the phenomenon of conduction, and permits the diagnosis of labor as a function of the signals. The stimulation of the vagina may either be electrical, mechanical or pharmacological, for example through the cutaneous introduction of oxytocin to the patient.

The apparatus of the present invention includes at least one electrode that is applicable to an abdominal surface of the patient under analysis, an analog-to-digital converter, that is connected to the electrodes, and that converts electromyographic signals produced by the electrodes into digitized data which are indicative of electromyographic signals, a memory for storing the digitized signals, and a programmed computer for analyzing the stored digitized signals and for providing an indication of uterine electrical activity of the patient under analysis as a function of the stored digitized signals.

These and other features and advantages of the present invention will become apparent to those of ordinary skill in this technology with reference to the following detailed description and appended drawings.

BRIEF DESCRIPTION OF THE DRAWINGS

Various features and attendant advantages of the present invention will be more fully appreciated as the invention becomes better understood when considered in conjunction with the accompanying drawings, in which like referenced characters designate the same or similar parts throughout the several views, and wherein.

DETAILED DESCRIPTION

Figure 1:
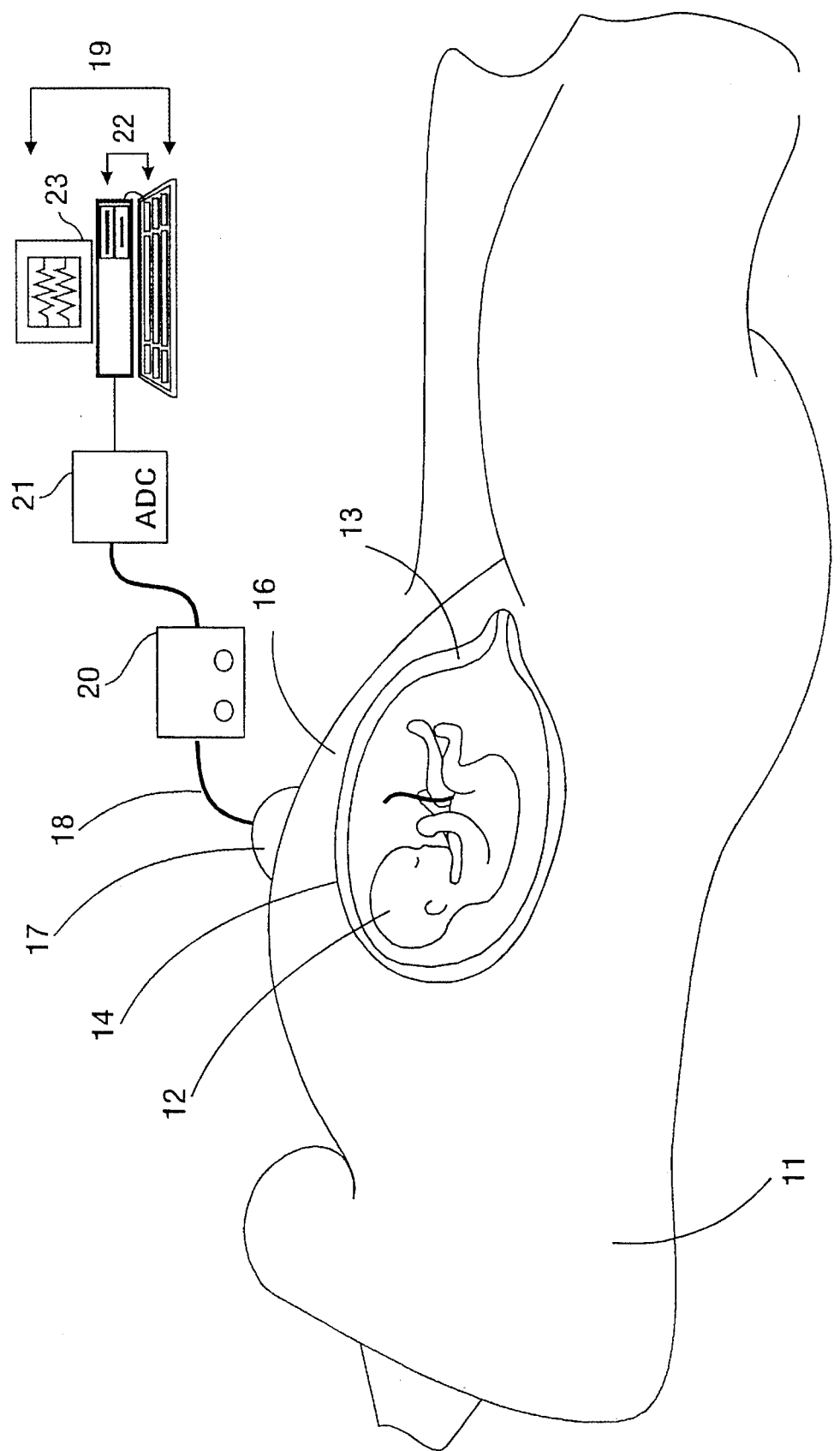
FIG. 1 is a side view, partially in phantom, showing the recording apparatus in accordance to the present invention attached to the abdominal wall of a pregnant patient.

Referring now to FIG. 1, there is shown schematically a pregnant patient 11 with a fetus 12 retained within the uterus 13. The uterine wall 14 is primarily configured of muscle tissue and is disposed proximate the abdominal wall 16 of the patient 11. In accordance with the principles of the present invention, electrodes 17 are placed on the exterior of the patient 11 on the abdominal wall 16. The electrodes 17 have leads 18 that are connected to a recording apparatus 19 including an amplifier 20, analog-to-digital converter (ADC) 21, computer 22 and monitor 23.

In accordance with the principles of the present invention, the uterus 13 of the pregnant patient 11 is monitored for electrical activity from signals detected on the surface of the abdomen. The signals (EMG) are amplified by amplifier 20, digitized by ADC 21, and displayed on a monitor 23. The signals are also stored in the memory of computer 22 for analysis of the frequency duration and other characteristics of the action potentials.

In accordance with one embodiment of the present invention, ADC 21 may be, for example, a Data-Pack II A/D board, available from Run Technologies, or a MacLab A/D board, available from MacLab Division of AD Instruments. Amplifier 20 may be, for example, a Grass polygraph recorder, Mode #7D with DC amplifiers, available from Grass Instruments, or a Gould amplifier and recorder Model TA240, available from Gould Instruments, or a MacLab amplifier for Macintosh computers, available from the MacLab Division of AD instruments. Computer 22 with monitor 23 may be, for example, any IBM PC compatible computer, preferably with a 486-type microprocessor and color display, or a Macintosh IIci computer with display, or a Mackintosh Powerbook laptop computer, or an IBM laptop computer, or any other equivalent computer and monitor.

Electrodes 17 may be, for example, stainless steel clips or cups, for example, various models available from Hewlett-Packard, silver or platinum clips or cups, or they may be a Bard catheter with electrodes for vaginal recording, available from Bard Reproductive Sciences.

Figure 2:
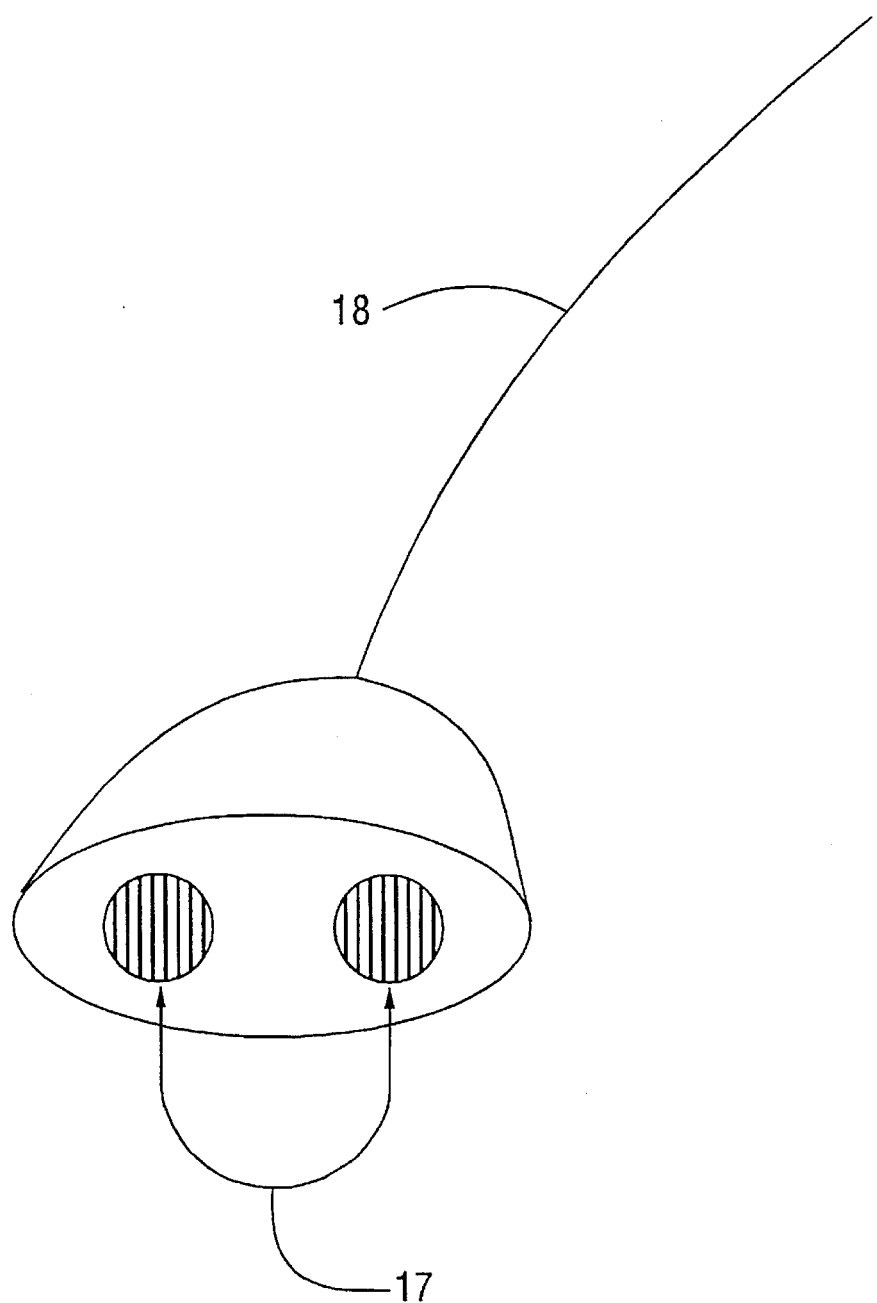
FIG. 2 is an enlarged view of the surface electrodes used in FIG. 1 in accordance with the present invention.

Although specific examples have been given for the various hardware components shown in FIG. 1, it will be understood that different hardware components may be used, without departing from the spirit and scope of the present invention. Referring also to FIG. 2, an enlarged side view of the electrodes 17 is shown, that are used in contact with a patient's abdominal wall. The electrodes 17 are bipolar (or tripolar) comprised of silver or platinum, and are spaced about 1 cm apart. Leads 18 from the electrodes 17 are connected to amplifier 20. The amplifier 20 includes controls for amplifying or attenuating the signals and also filters for elimination of some of the high or low frequency noise. The amplifier is, for example, a battery powered ac/dc differential amplifier with the following approximate specifications:

| Gain, AC and DC | ×100, ×1,000 & ×10,000 |
|---|---|
| Input resistance | $10^{12}$ ohms typical |
| Leakage current | 50 pA typical |
| Common Mode Rejection | 100,000: 1 min @ 60 Hz |
| Noise, input shorted | 10 μV p-p, 1 Hz–10 kHz |
| Low Freq filter settings | 0.1, 1.0, 10, 300 Hz |
| High Freq filter settings | 0.1, 1.0, 3.0, 10 kHz |
| Output resistance | 220 ohms |

The computer 22 and monitor 23 may be of conventional PC design with software and hardware to digitize the signals. The computer 22 is programmed with software to enable computer 22 to store, display and analyze the signals. The operation of computer 22, in accordance with the present invention, is discussed below in detail with reference to the flow charts of FIGS. 4A–4E.

Figure 3:
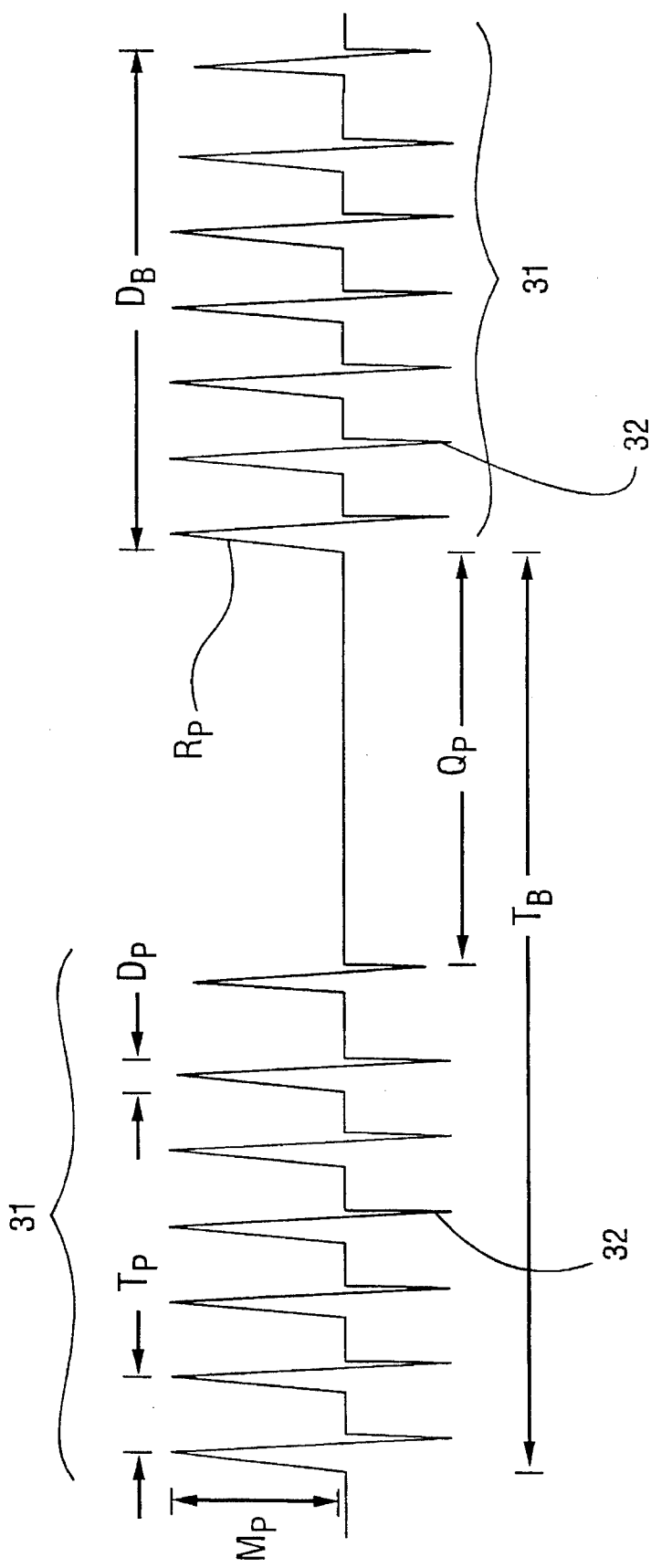
FIG. 3 is an illustration of two bursts of action potentials of an EMG signal.

Referring also to FIG. 3, shown are typical bursts 31 that are composed of multiple action potentials 32 recorded from the surface of a patient's abdomen 16 from electrical activity of the uterus 13 and that correspond to the overlying contractility of the uterus 13 (see also, FIG. 1). Various parameters are measured from the bursts and from the action potentials, and are used for diagnostic purposes in accordance with the present invention. These parameters include: Frequency of bursts($1/T_B$), number of bursts per unit time ($N_B$), duration of bursts ($D_B$), quiescent periods between bursts ($Q_P$), number of action potentials in each burst ($N_P$), and characteristics of the action potentials including, frequency of action potentials ($1/T_P$), duration of action potentials ($D_P$), magnitude of action potentials ($M_P$), rate of rise of action potentials ($R_P$, i.e. slope of the depolarization of action potentials, dv/dt).

Referring now to FIGS. 4A–4E, presented are flow charts depicting the operation of the apparatus of FIG. 1, in accordance with the present invention. In practice, the flow charts of FIGS. 4A–4E are embodied in a computer program used to control the operation of computer 22 of FIG. 1. Beginning in step 41, computer 22 acquires EMG signals produced by electrodes 17, which have been amplified by amplifier 20 and digitized by ADC 21. In step 42, digitized versions of the EMG signals are stored in the memory of computer 22.

Control then passes to step 43 where the stored EMG data is analyzed to assess parameters reflecting groups or bursts of action potentials present in the stored EMG signal. These analysis steps are shown in more detail with reference to FIG. 4B. Control then passes to block 44 wherein the stored EMG signal is analyzed to determine parameters characterizing the individual action potentials within the stored EMG signal. The details of the action potential analysis is shown in FIG. 4C.

Control then passes to step 46 where probability analysis is conducted on the EMG signal characteristics determined in steps 43 and 44. The details of this probability analysis are shown with reference to FIG. 4D.

Control then passes to decision block 47 where, based upon the probability analysis performed in step 46, it is determined whether the stored EMG signal reflects normal or abnormal uterine progression. The details of this diagnostic decision are shown below with reference to FIG. 4E.

If normal progression is concluded by decision block 47, control passes to block 48 wherein the normal progression is characterized as either non-labor, prelabor or labor based upon characteristics of the bursts and action potentials. If abnormality is concluded by decision block 47, control passes to block 49 where the abnormality is characterized as preterm labor, dystocia or other abnormalities based upon characteristics of abnormal bursts and action potentials.

Figure 4A:
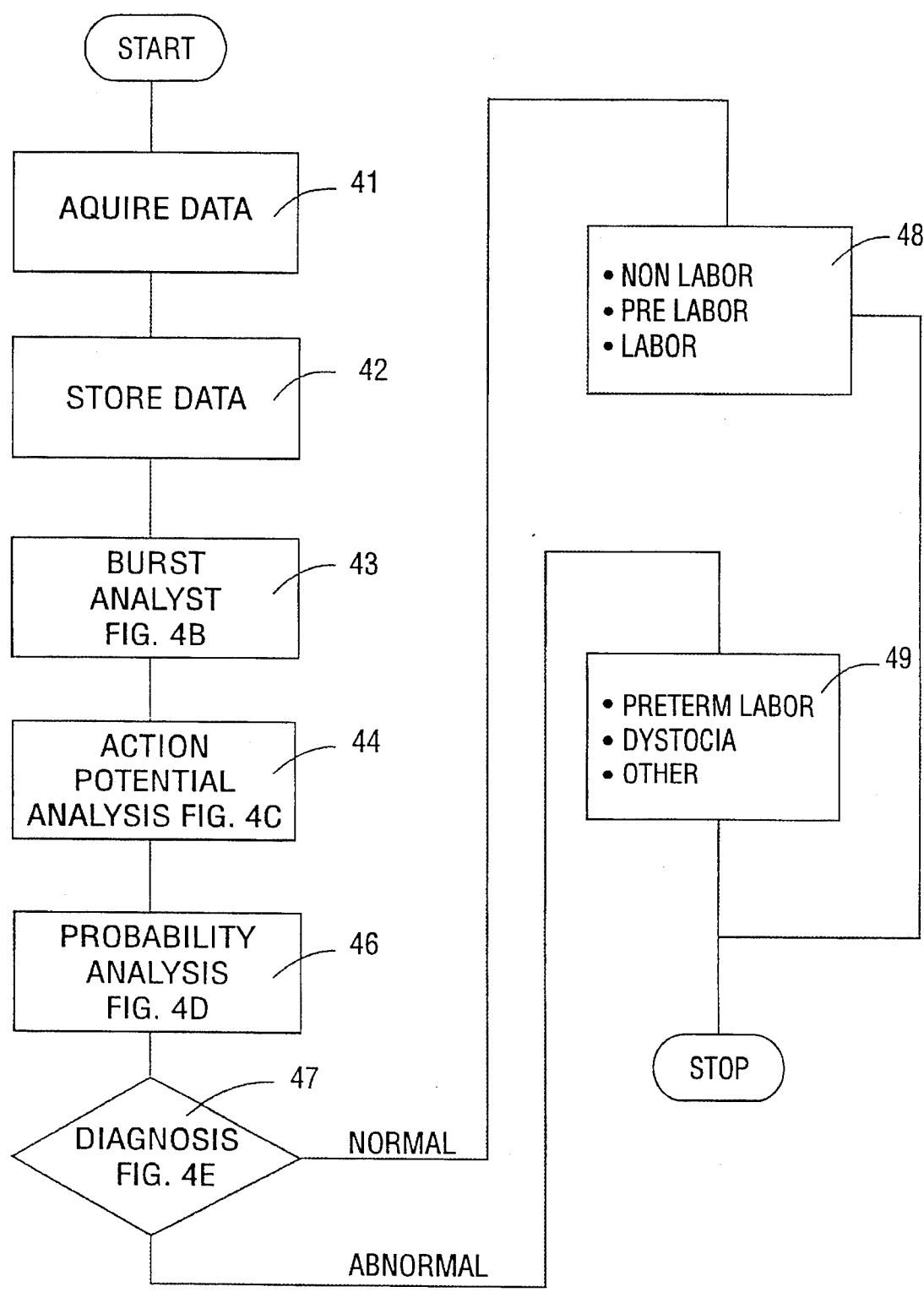
FIG. 4A–4E are flow charts of the method of the present invention.
Figures 4B, 4C:
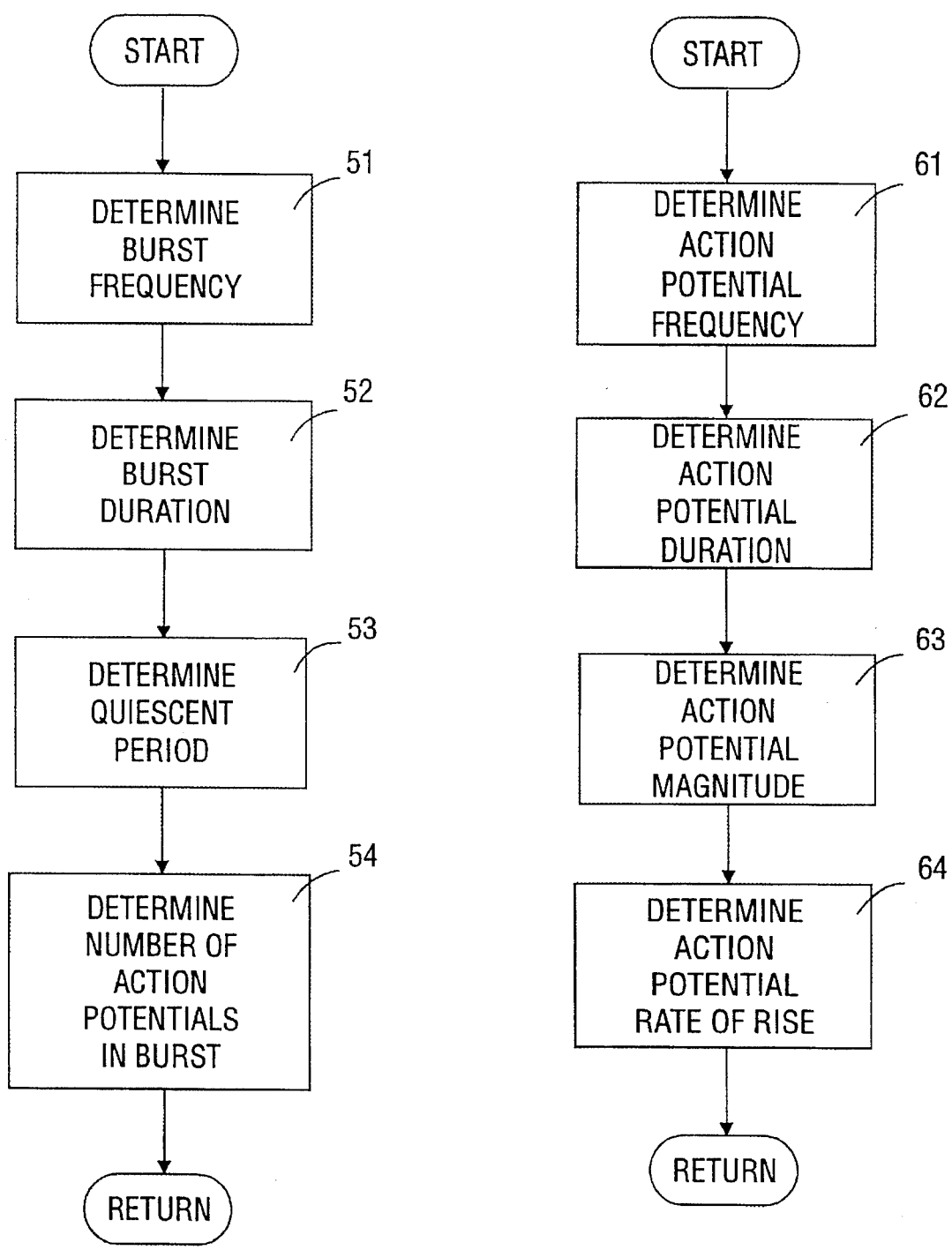

Referring now to FIGS. 3 and 4B, the details of the analysis of burst activity conducted within block 43 of FIG. 4A are presented. Beginning in step 51, the frequency of each burst ($1/T_B$) is determined by estimating the number of bursts per unit time, control then passes to block 52 where the duration of each burst ($D_B$) is determined by measuring the time from the first action potential of the burst until the final action potential of the burst. Then, in block 53, the quiescent periods ($Q_P$) between the bursts are determined from measurements of the last action potential in a burst to the first action potentials in another burst. Then, in block 54, the number of action potentials in each burst ($N_P$) are determined Control is then returned to the flow chart of FIG. 4A.

FIG. 4C presents the details of the analysis of action potential performed by block 44 of FIG. 4A. Beginning in block 61, the frequency of the action potential ($1/T_P$) is determined by estimating the number of action potentials per unit time within each burst. Then, in block 62, the duration of the action potentials ($D_P$) is determined by measuring the time from depolarization to repolarization. Control then passes to block 63 where the magnitude of the action potentials ($M_P$) is determined from measurements of the peak voltage of the depolarization. Control then passes to block 64 where the rate of rise of the action potentials ($R_P$) is determined by determination of the slope dv/dt of depolarization. Conduction is estimated in a known manner from the rate of rise of action potentials ($R_P$). In general, the greater the rate of rise, $R_P$, the higher the conduction. Conduction may also be estimated from analysis of data when more than one surface electrode is used and time between bursts from separate electrodes is estimated or after vaginal stimulation (see below). Control then returns to the flow chart of FIG. 4A.

Figure 4D:
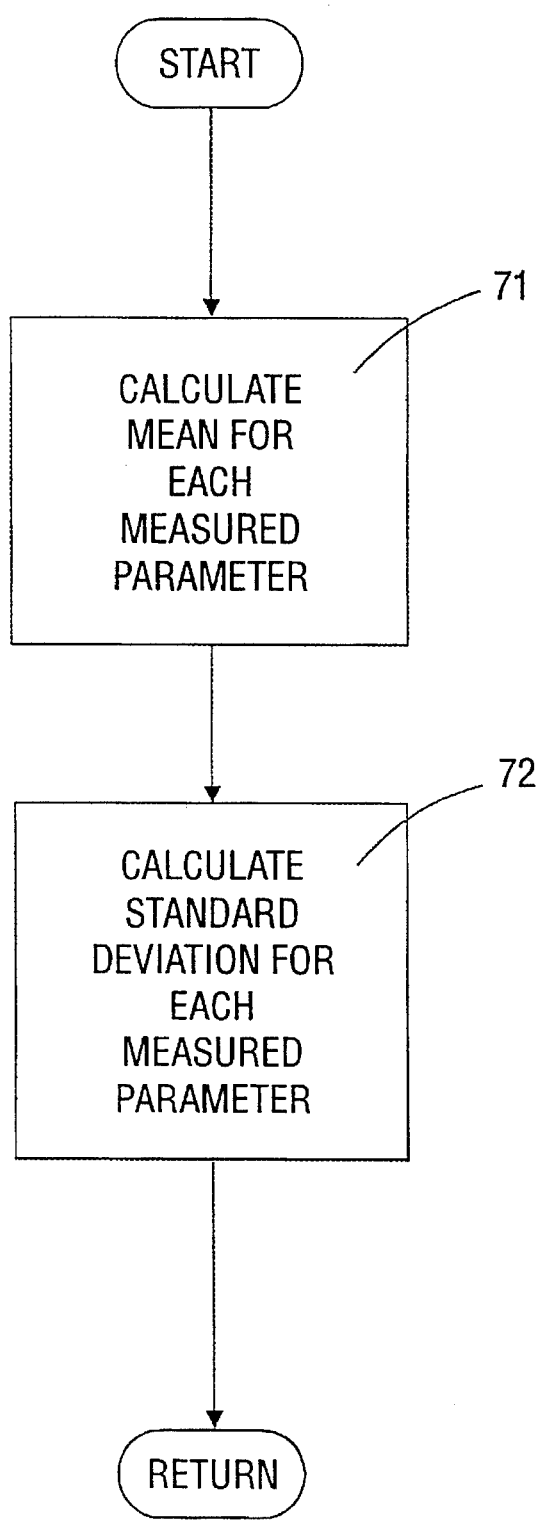

FIG. 4D shows details of the probability analysis performed by block 46 of FIG. 4A. Beginning in block 71, the mean of each of the measured parameters is determined (see also, FIGS. 4B and 4C), and the standard deviation of each of the parameters is calculated.

Figure 4E:
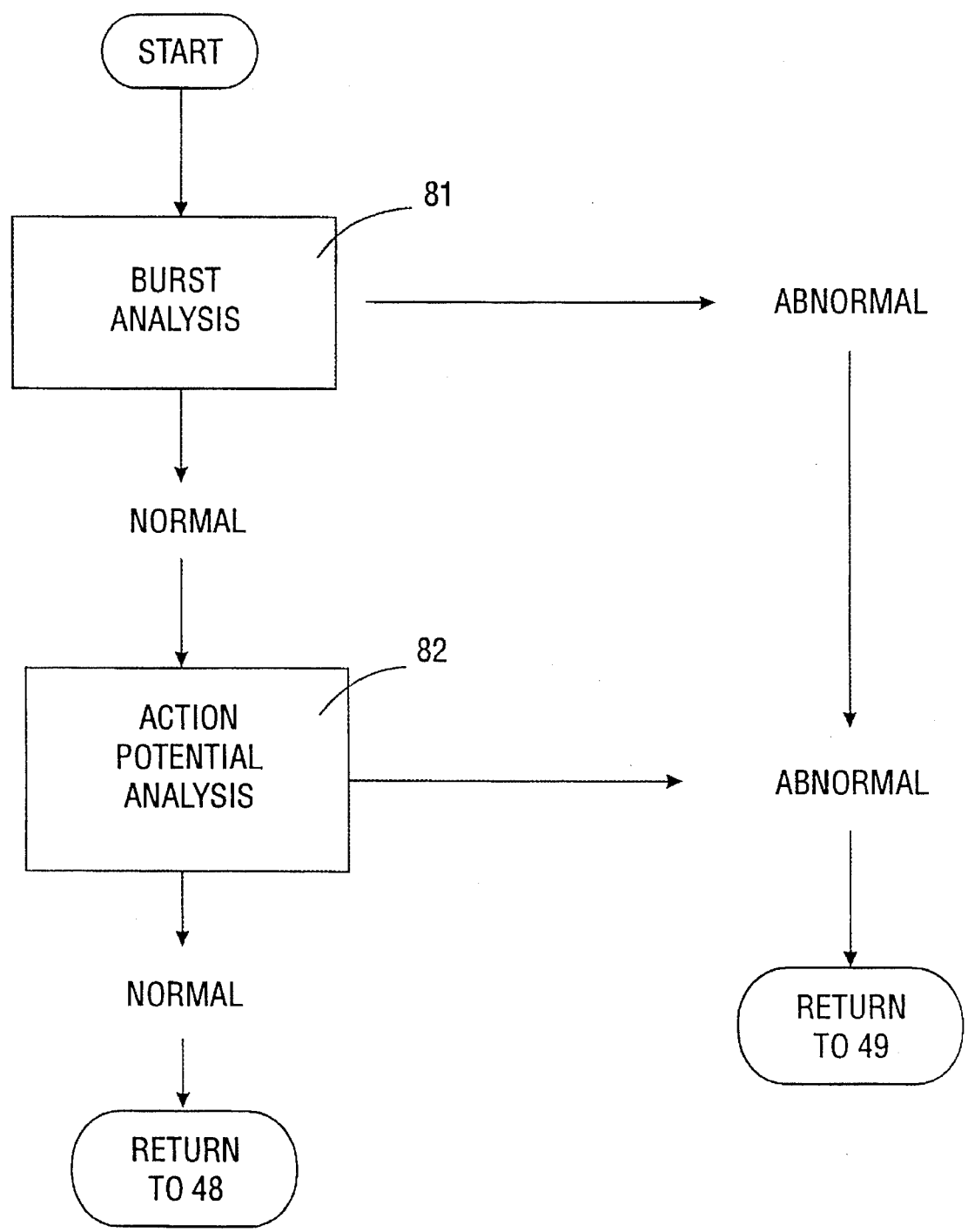

FIG. 4E presents the details of the diagnosis step (block 47). Data from burst and action potential probability analysis (block 46) pass to blocks 81 and 82 respectively and recorded burst and action potentials are compared to known normal ranges of values. Estimates for normal values for the measured parameters for action potentials and bursts of action potentials for labor patients are presented in the following tables.

ACTION POTENTIALS

Frequency: 1/second
Duration: 100 milliseconds
Amplitude: 1 millivolt

BURSTS

Frequency: 0.5–2.0/minute
Duration: 10–30 seconds
Action Potentials/Burst: 20

For non-labor patients, considerably lower values for the measured parameters for action potentials and bursts of action potentials are considerably lower than the values presented in the above tables, with the exception of burst duration which may actually be larger. For values either higher or lower than normal for burst or action potential data, the computer recognizes these as abnormal and passes control to block 49. If burst or action potential parameters are within normal limits, the information passes to block 48. The calculated standard deviations for the measured parameters are used to determine whether the calculated parameter means for statistically different or the same as normal values.

While utilization of the apparatus and method has been described above as particularly useful for monitoring the uterine wall during pregnancy, the instrument can also be used to measure electrical activity from the vagina that propagates or conducts from the uterus. This is particularly useful in early pregnancy or in nonpregnant patients where the uterus is small and not in contact with the abdominal wall. In addition, it is within the scope of this invention to utilize the apparatus and method thereof for medical and biological procedures other than uterine wall monitoring, such as, for example bladder or bowel function.

From the foregoing description, one skilled in the art may easily ascertain the essential characteristics of this invention, and without departing from the spirit and scope thereof, may make various changes and modifications of the invention to adapt it to various usages and conditions.

FIG. 5–14 illustrate use of the present for monitoring uterine electrical activity. To produce the graphs of FIG. 5–14, bipolar electrodes were placed on the abdominal surface of pregnant rats to monitor EMG activity in accordance with the present invention. In addition, in order to demonstrate the efficacy of the present invention relative to prior, more invasive, procedures, stainless steel electrodes were implanted directly on the uterus and/or vagina wall surface, and, a pressure transducer (specifically, a Model SPR-524 transducer available from Millar Instruments of Houston, Tex.) was placed in the uterus. The apparatus for recording was identical to that described above. The above described invention is designed for use mainly in humans or domestic animals whereas the following FIGS. 5–14 represent data obtained from rats. The instrumentation is essentially the same for both species.

FIGS. 5–14 illustrate the correlation between the EMG signals recorded by the abdominal surface electrodes of the present invention, and signals recorded from uterus electrodes surgically implanted in the uterus.

Figure 5:
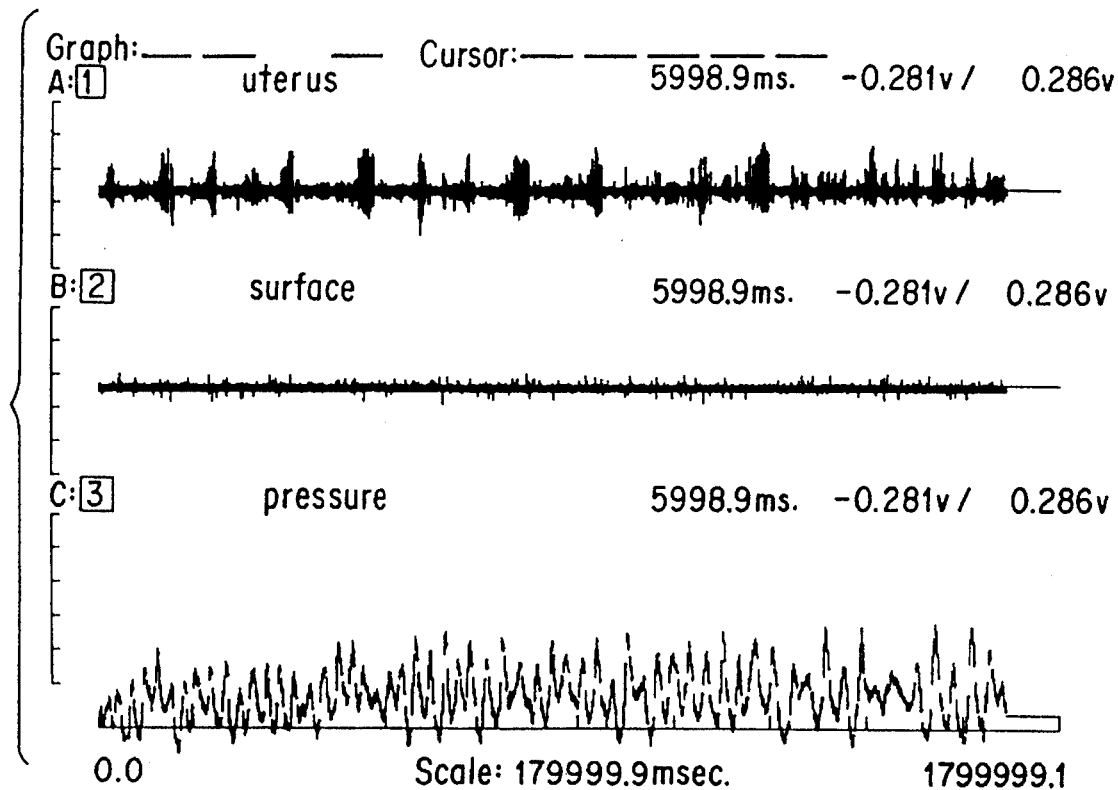
FIG. 5–14 are graphs of EMG signals, illustrating the present invention.
Figure 6:
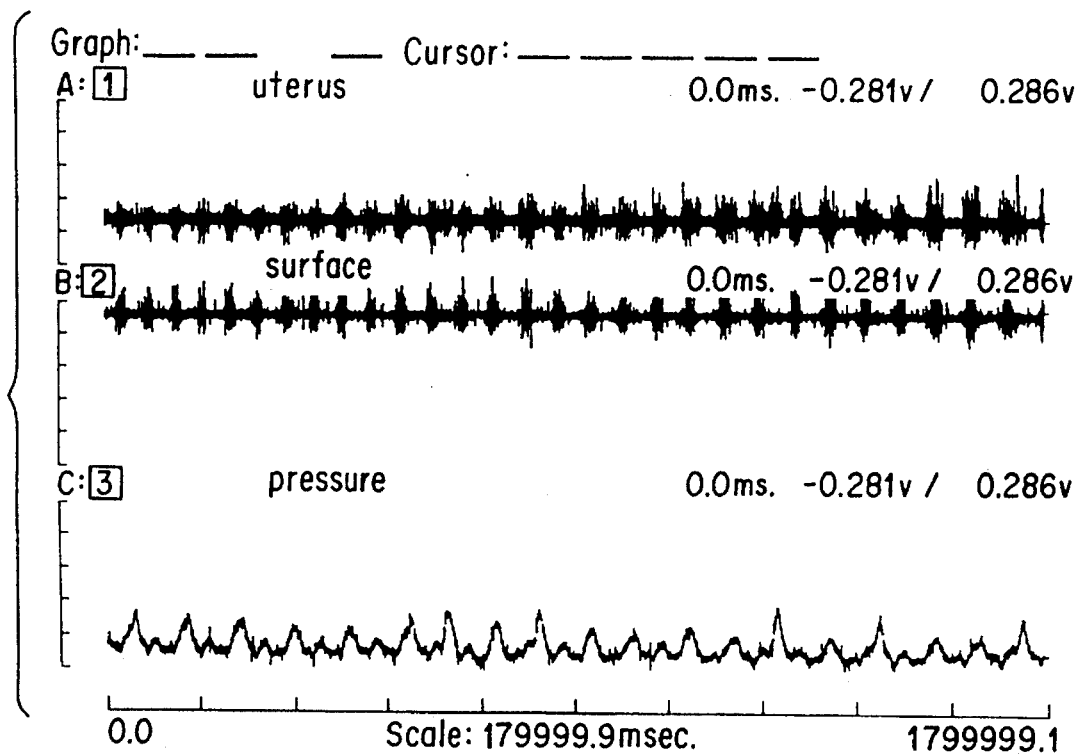
Figure 7:
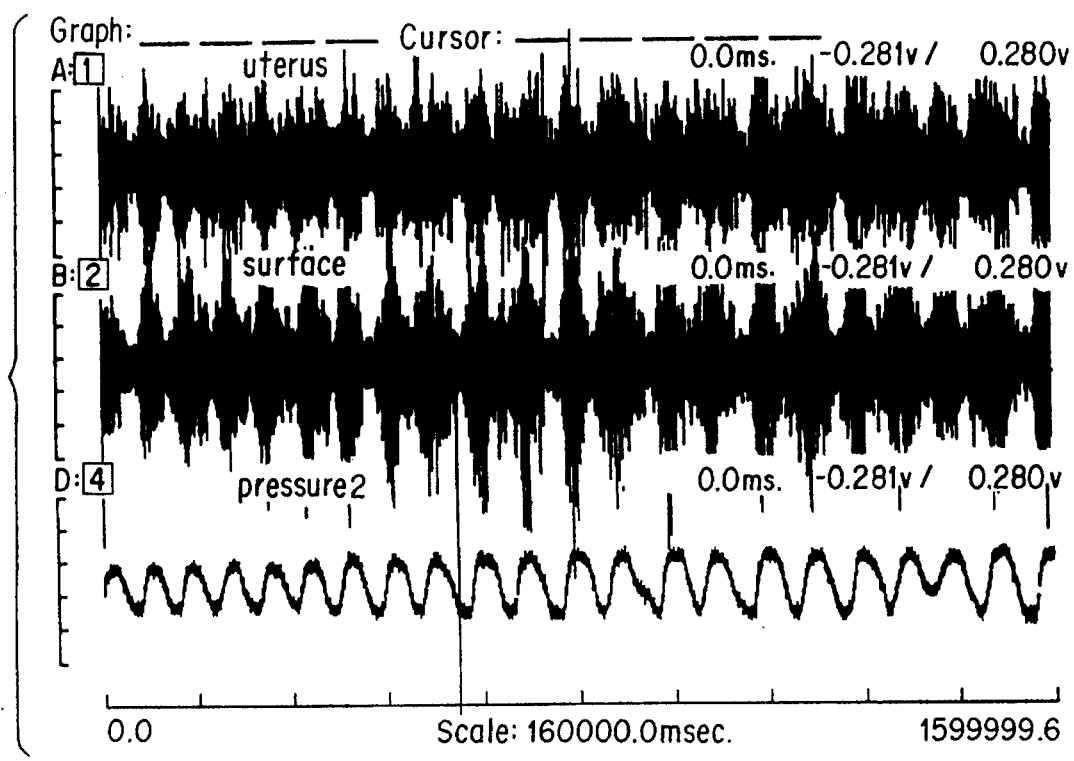

FIGS. 5, 6 and 7 show EMG activity (electrical activity of the uterus) (Channels 1 and 2) and pressure (Channel 3) recorded simultaneously directly from the uterine wall (Channel 1) and from the abdominal surface (Channel 2) of pregnant rats. Pressure (Channel 3) was measured from an intrauterine pressure device. Note that on days 18 and 21 of gestation (FIGS. 5 and 6) bursts of electrical activity are small and do not always correspond on the surface and uterus (FIG. 5, Channels 1 and 2), but do coincide with small uterine contractions (FIGS. 5 to 7, Channel 3). On the other hand, at term during delivery (FIG. 7) the EMG bursts signals from both the uterus and abdominal surface are of high amplitude and correlate with large pressure changes.

These studies indicate that uterine EMG activity is low prior to term and that it increases dramatically during labor and delivery. Furthermore, these data show that uterine electrical activity may be recorded from the abdominal surface (Channel 2) to give an adequate representation of either the uterine electrical or mechanical activity.

Figure 8:
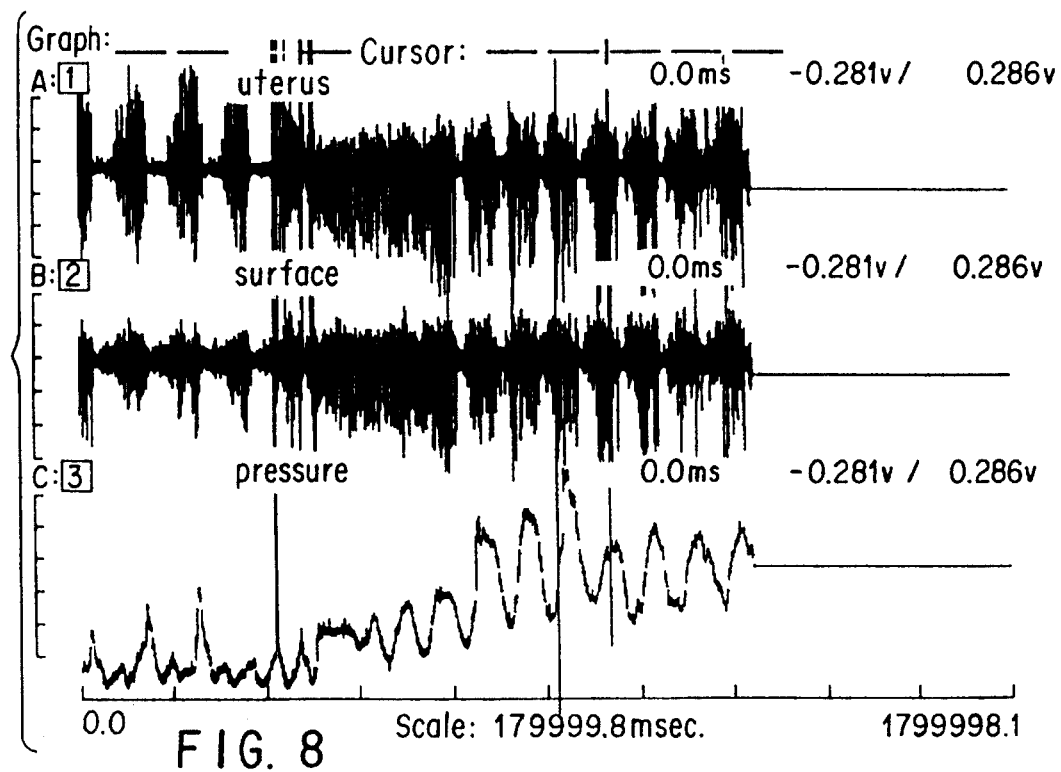

FIG. 8 shows EMG and pressure recordings from an animal during labor at term before and after treatment with oxytocin. Note that the bursts (Channels 1 and 2) coincide to low pressure changes (Channel 3) prior to oxytocin. Following IV infusion of oxytocin the EMG activity as recorded on the uterus (Channel 1), and abdominal surface (Channel 2) increase substantially and correspond to the large pressure changes in the uterus. These results indicate that electrical activity recorded from the surface of the abdomen (Channel 2) accurately mirrors changes in uterine EMG activity (Channel 1) and uterine pressure (Channel 3).

Figure 9:
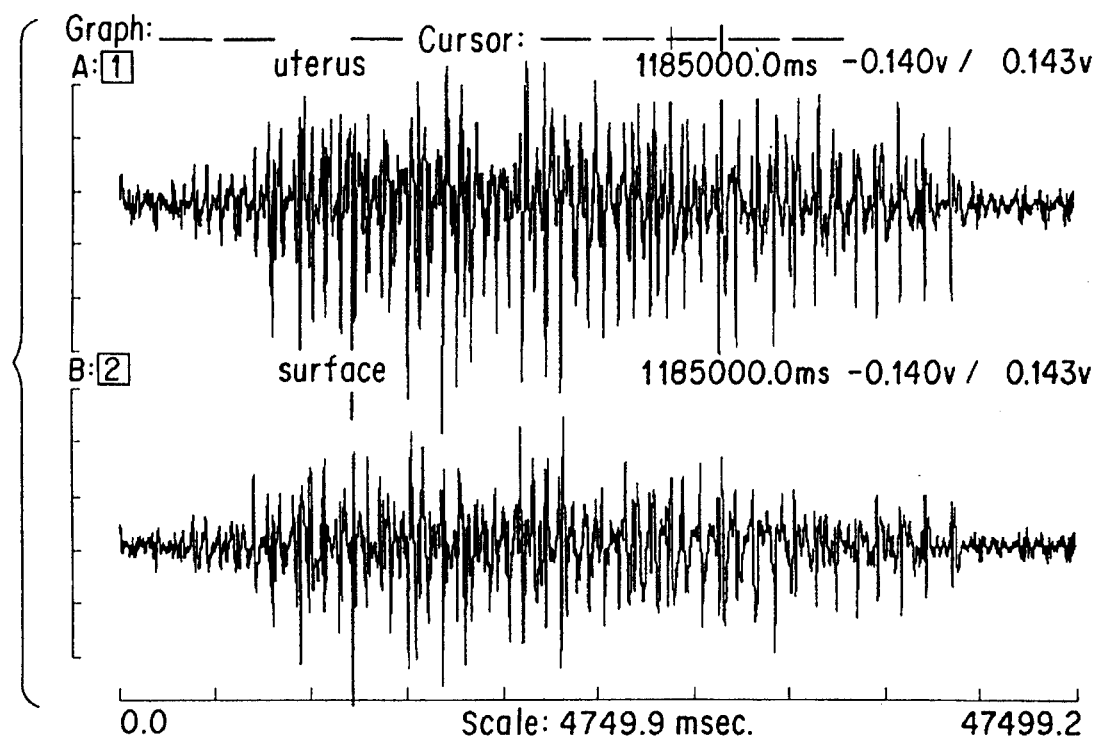

FIG. 9 shows an expanded portion of an EMG burst recorded from the uterus (Channel 1) and abdominal surface (Channel 2). Note that the individual action potentials within the bursts correspond between those recorded from the uterus and surface.

Figure 10:
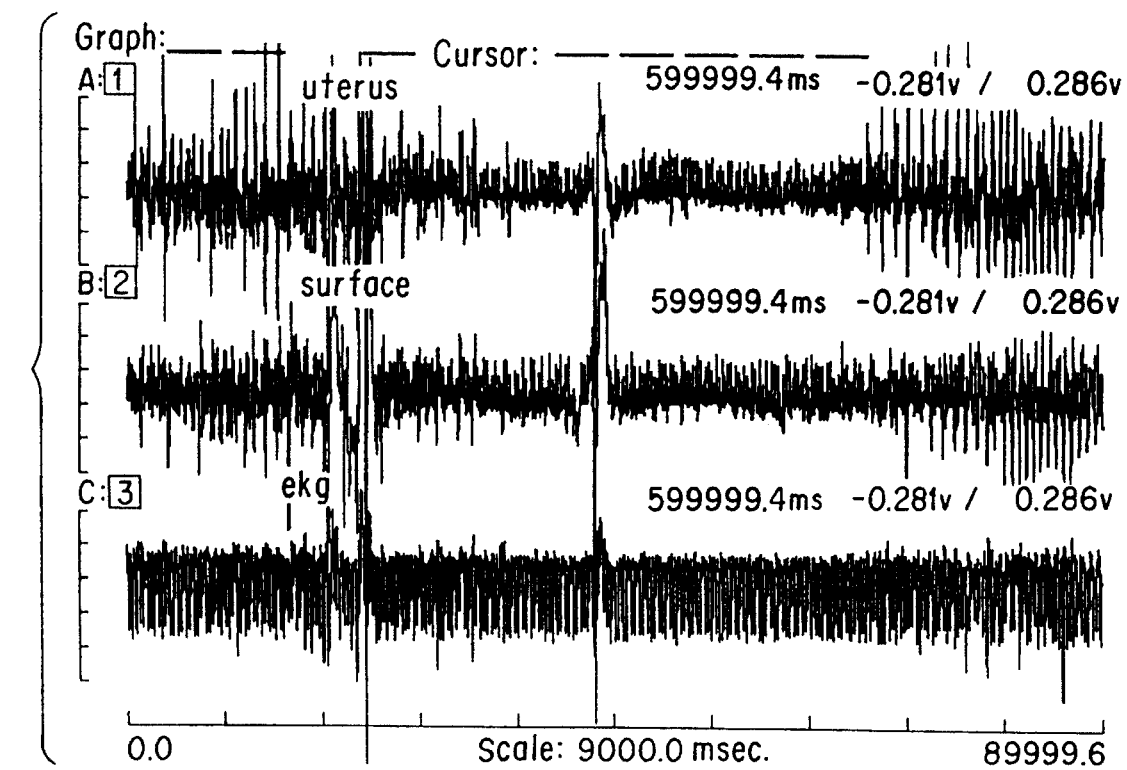

FIG. 10 illustrates EMG activity recorded from the uterus (Channel 1), abdominal surface (Channel 2) and activity of the heart (recorded with external electrodes placed on the chest) (Channel 3). Note that cardiac action potentials occur regularly with a frequency which matched the heart rate (300 to 400 beats per minute). In contrast bursts of action potentials from the uterus recorded with both uterine and abdominal surface electrodes occur periodically. Note that a minor signal from the cardiac potentials appears in the EMG signals from the uterus and uterine signals overlap with some signals from the heart. This information shows that one can record action potential bursts from the uterus with surface electrodes on the abdomen with little interference from the heart.

Figure 11:
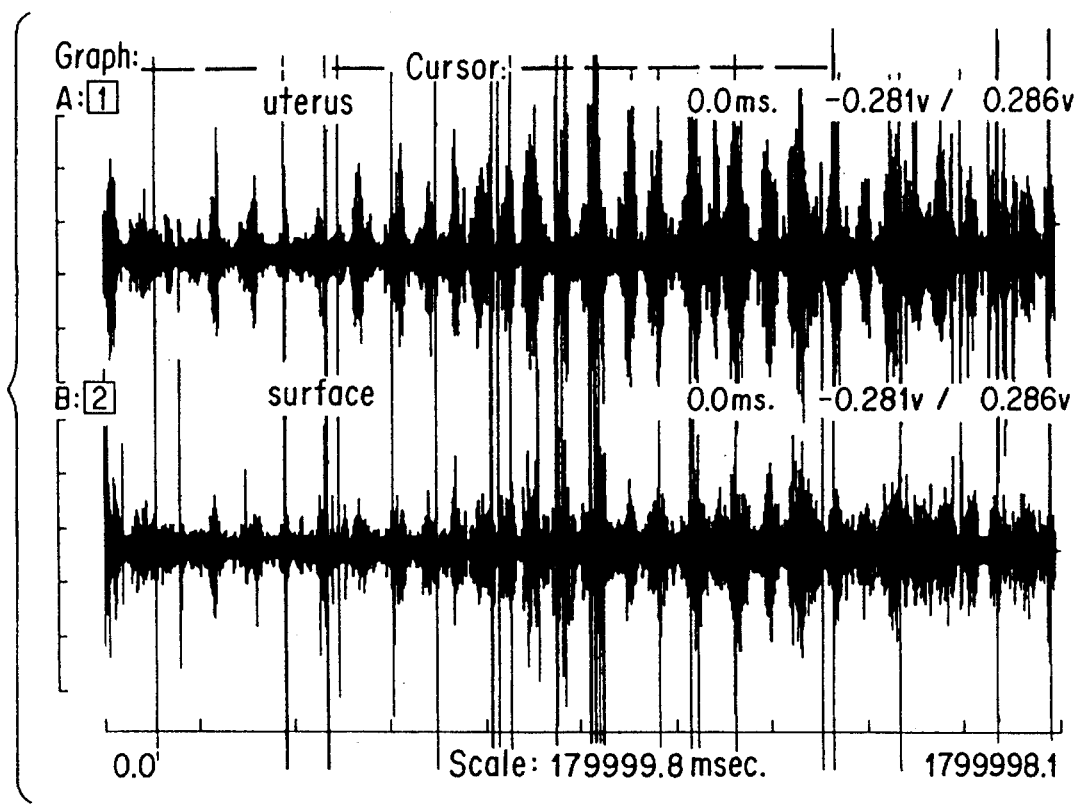

FIG. 11 demonstrates EMG recordings from the uterus and abdominal surface in conscious rats (FIGS. 5 to 10 and FIG. 12 show data from anesthetized animals). Shown are corresponding bursts of EMG activity demonstrating that it is possible to record uterine electrical signals from the abdominal surface from conscious animals.

Figure 12:
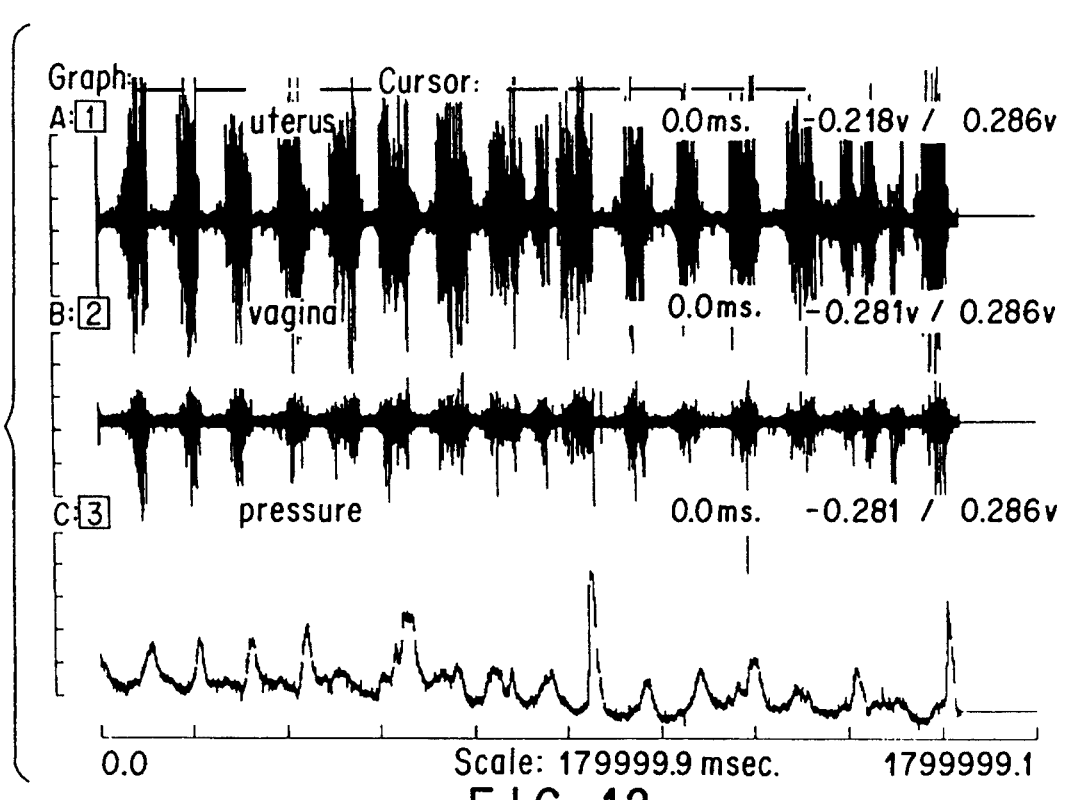

FIG. 12 shows EMG recordings from the uterus (Channel 1) and vagina surface (Channel 2) and intrauterine pressure (Channel 3). Note the correspondence between uterine and vaginal EMG activity with accompanying changes in intrauterine pressure. These studies indicate that it is possible to record uterine EMG activity from the vaginal wall.

Figure 13:
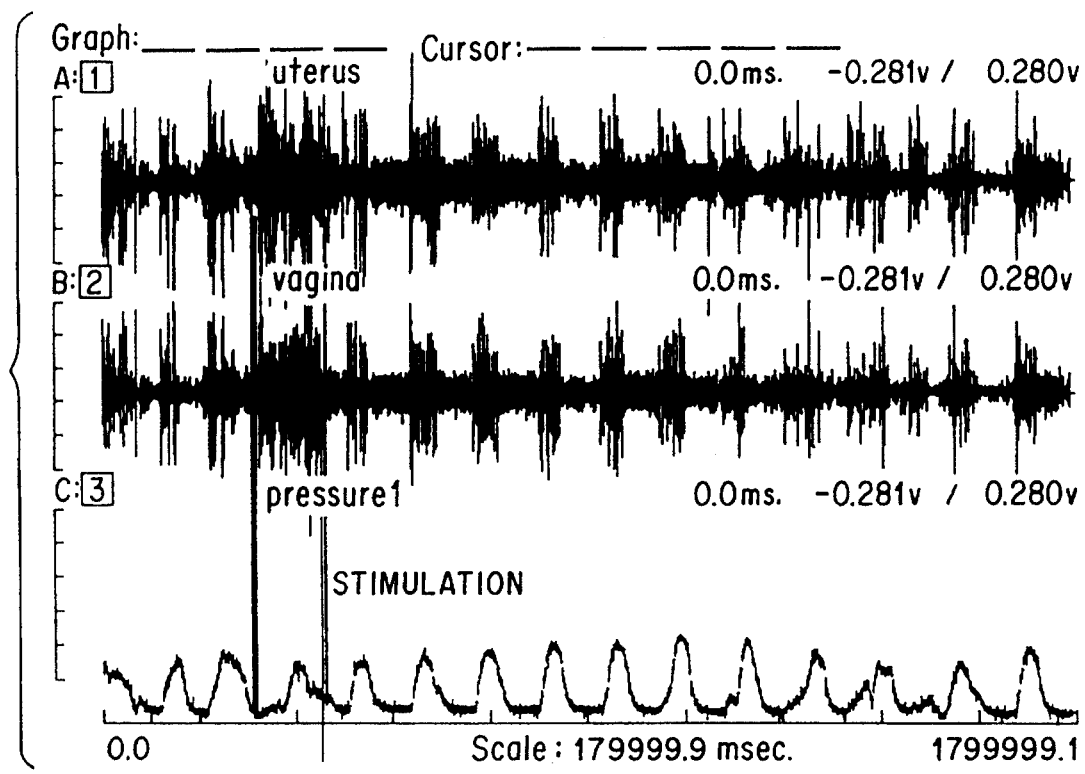
Figure 14:
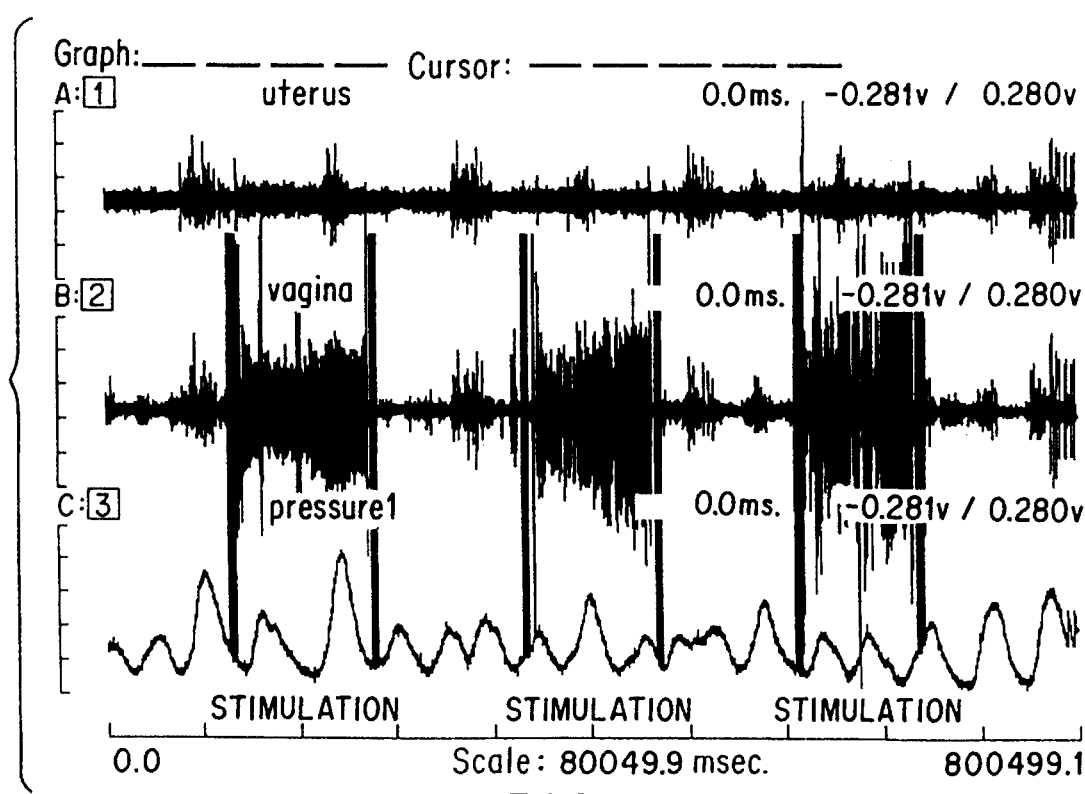

FIGS. 13 and 14 depict a portion of EMG signals recorded from the uterus (Channel 1) and from the vaginal surface (Channel 2), indicating that when the vagina is stimulated mechanically during labor, signals are propagated (conducted) to the uterus (FIG. 13), whereas when the vagina is mechanically stimulated prior to term, signals are not conducted to the uterus (FIG. 14). This assessment of conduction may be used to indicate or diagnose a state of preparation for labor.

The present method and apparatus may also be used to measure normal and abnormal function of other smooth muscle tissue, such as that of the bladder and lower gastrointestinal tract. Both organs depend upon smooth muscle contractility to perform their respective functions. Thus, electrical activity of the bladder and bowel may be registered from the abdominal surface during respective urination or defecation, in order to estimate appropriate and abnormal electrical activity of these organs.

While the present invention has been presented with reference to particular embodiments, it will be understood that additions, deletions and changes to these embodiments may be made without departing from the spirit and scope of the present invention.

What is claimed is:

1. A method of characterizing uterine electrical activity, comprising:

applying action potential measuring electrodes to an abdominal or vaginal surface of a patient;

storing electromyographic signals, including action potentials, produced by said electrodes;

analyzing uterine activity indicating parameters from action potentials within said stored electromyographic signals; and characterizing uterine activity of said patient based on said parameter analysis.

2. The method of claim 1, further comprising:

stimulating a vagina of said patient while said electromyographic signals are being stored; and diagnosing labor as a function of said parameter analysis.

3. The method of claim 2, said stimulating step comprising, mechanically stimulating said vagina.

4. The method of claim 2, said stimulating step comprising, pharmacologically stimulating said vagina.

5. The method of claim 2, said stimulating step comprising electrically stimulating said vagina.

6. The method of claim 2, said diagnosing step comprising, assessing conduction of action potentials in said uterus as a result of said stimulating step.

7. The method of claim 1, said analyzing step comprising, calculating a burst frequency of action potentials in said stored electromyographic signals.

8. The method of claim 7, said characterizing step comprising, characterizing said uterine activity by comparing said calculated burst frequency with a predetermined threshold.

9. The method of claim 1, said analyzing step comprising, calculating a frequency of action potentials within a burst of action potentials in said stored electromyographic signals.

10. The method of claim 9, said characterizing step comprising, comparing said calculated frequency of action potentials with a predetermined threshold.

11. The method of claim 1, said analyzing step comprising, calculating a duration of bursts of action potentials within a said stored electromyographic signals.

12. The method of claim 11, said characterizing step comprising, comparing said calculated burst duration with a predetermined range.

13. The method of claim 1, said analyzing step comprising, calculating a number of action potentials within each burst of action potentials in said stored electromyographic signals.

14. The method of claim 13, said characterizing step comprising, comparing said calculated number of action potentials within each burst with a predetermined threshold.

15. The method of claim 1, said analyzing step comprising, calculating a magnitude of action potentials within said stored electromyographic signals.

16. The method of claim 15, said characterizing step comprising, comparing said calculated magnitude of action potentials with a predetermined threshold.

17. The method of claim 1, said analyzing step comprising, calculating a rise time of action potentials within said stored electromyographic signals.

18. The method of claim 17, said characterizing step comprising, characterizing conduction of action potentials as a function of said calculated rise time.

19. An apparatus for recording and analyzing uterine electrical activity from the abdominal or vaginal surface, comprising:

at least one action potential measuring electrode applicable to an abdominal or vaginal surface of a patient under analysis;

an analog-to-digital converter, connected to said at least one electrode, for converting electromyographic signals, including action potentials, produced by said electrode into digitized data indicative of said electromyographic signals and action potentials;

a memory for storing said digitized data; and a programmed computer for analyzing uterine activity indicating parameters from action potentials represented by said stored digitized data, and for providing an indication of uterine electrical activity of said patient under analysis as a function of said uterine activity indicating parameters.

* * * * *